United States Patent [19]

Magers

[11] Patent Number: 4,915,216
[45] Date of Patent: Apr. 10, 1990

[54] SURGICAL BOWL

[76] Inventor: Paul E. Magers, c/o Alpha Industries, Inc., P.O. Box 808, 701 North Greenwood Ave., Clearwater, Fla. 33517-0808

[21] Appl. No.: 366,334

[22] Filed: Jun. 14, 1989

Related U.S. Application Data

[63] Continuation of Ser. No. 290,554, Dec. 27, 1988, abandoned.

[51] Int. Cl.⁴ .................. B61B 17/04; B65D 21/02
[52] U.S. Cl. ................................. 206/520; 206/63.3
[58] Field of Search ............... 206/503, 515, 519, 520, 206/63.3

[56] References Cited

U.S. PATENT DOCUMENTS

| | | | |
|---|---|---|---|
| 3,393,826 | 7/1968 | Brown | 206/520 |
| 3,495,703 | 2/1970 | Calabrese | 206/63.3 |
| 3,934,725 | 1/1976 | Edwards | 206/520 |
| 4,231,476 | 11/1980 | Compton | 206/520 |

FOREIGN PATENT DOCUMENTS

| | | | |
|---|---|---|---|
| 74647 | 4/1954 | Netherlands | 206/63.3 |
| 1355121 | 5/1974 | United Kingdom | 206/520 |

Primary Examiner—George E. Lowrance
Attorney, Agent, or Firm—Biebel, French & Nauman

[57] ABSTRACT

A bowl for temporarily storing a coiled wire to be used to guide a catheter into the heart of a patient includes a plurality of angularly spaced lugs projecting inwardly from the inner surface thereof at a location near the vertical center of the bowl to define a space therebelow for receiving the coiled wire. When the bowl is filled with heparin solution up to the level of these lugs and the coiled wire is placed therein below the lugs, it is effectively retained against accidental emergence above the solution and is also protected against accidental kinking when it is withdrawn past the lugs for use. Special provision is made for facilitating the nesting of a plurality of the bowls for shipment or storage while protecting against damage of any of the lugs by the nesting of one bowl in another.

6 Claims, 1 Drawing Sheet

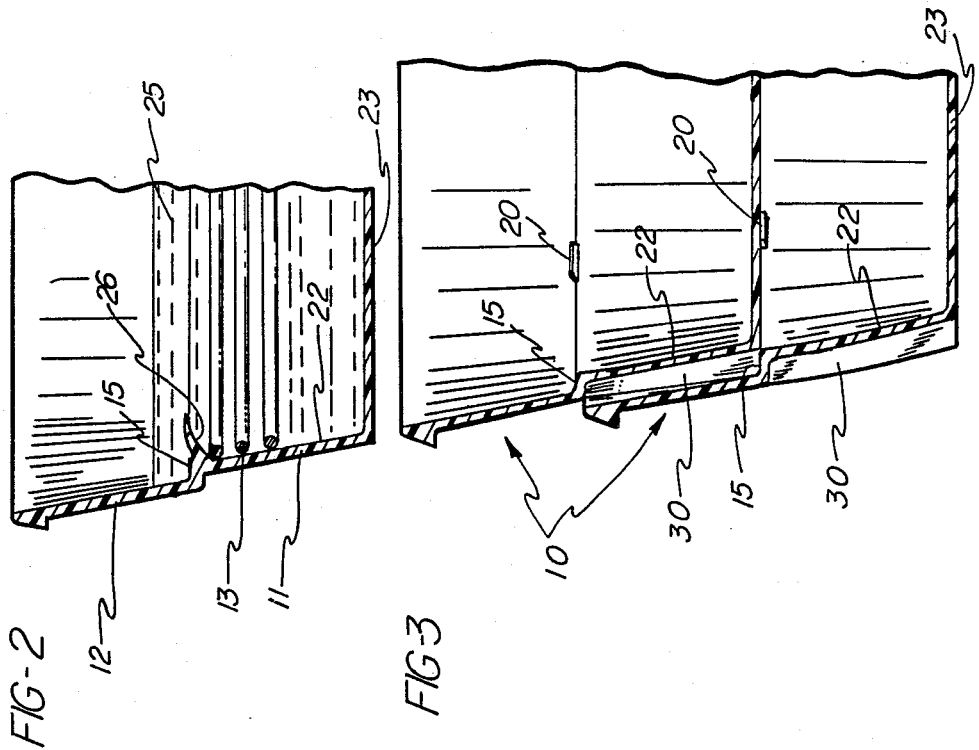
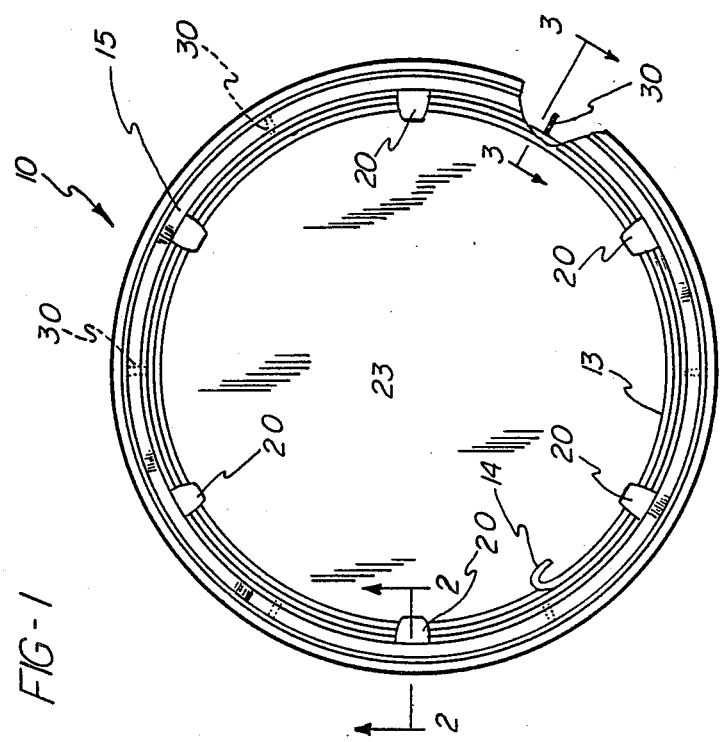
FIG-1
FIG-2
FIG-3

SURGICAL BOWL

This is a continuation of co-pending application Ser. No. 290,554, filed Dec. 27, 1988, and now abandoned.

BACKGROUND OF THE INVENTION

In surgical operations which involve the catheterization of the heart of a patient, it is a common practice to insert a flexible wire through a vein or artery into the heart and then to use that wire to guide a catheter into the heart. In addition to the fact that each such guide wire must of course initially be sterilized, it is also considered most desirable that immediately prior to its use, the wire be immersed in a heparin solution because of its anti-clotting effect on the blood with which the wire comes in contact during use.

It has also been a standard practice that any such wire, which may be of quite considerable length, e.g. 5 feet, be temporarily stored in the operating room in a bowl which contains a supply of heparin solution and into which the wire may be inserted in coiled condition. Bowls of such size and a convenient depth, e.g. 3 inches, are of course readily obtainable, but it appears that heretofore, the art has not provided such a bowl which includes any specific provision for assuring that the coiled wire will be retained below the level of the heparin solution until it is to be used. More specifically, it is understood that difficulties have been encountered in the past with the coiled wire, which is somewhat springy, tending to expand its coils sufficiently to rise above the level of the solution, so that portions thereof may not only lose their coating of the heparin solution but may even become contaminated by exposure to the surrounding atmosphere.

SUMMARY OF THE INVENTION

In accordance with the invention, these disadvantages of the prior practice are corrected or eliminated by the provision of a bowl which is especially constructed to retain a coiled guide wire for the above purpose in a heparin solution in such manner that no part of the wire can accidentally arise out of the solution but the wire is nevertheless readily available for removal and use when needed without the possibility of its becoming kinked before or during removal.

More specifically, the invention provides a bowl of substantially greater total depth than is actually needed for the purpose, and the inner surface of this bowl includes a plurality of angularly spaced lugs projecting inwardly at a location near the vertical center of the bowl which thereby define a space therebelow for receiving the coiled wire. Thus when the bowl is filled with heparin solution up to the level of these lugs and the coiled wire s placed therein below the lugs, it is effectively retained against accidental emergence above the solution, but it is readily withdrawn past the lugs when it is to be used.

Special provision is made for facilitating the nesting of a plurality of the bowls for shipment or storage while protecting against damage of any of the lugs by the nesting of one bowl in another. For this purpose, each bowl includes two integral sections, the lower of which is sufficiently smaller than the upper in inner diameter to provide an annular ledge within the bowl. The wire-retaining lugs project inwardly from the inner periphery of this ledge, and the outer surface of the lower portion of each bowl is provided with a plurality of radially projecting ribs proportioned to fit within the upper portion of another bowl during nesting and to seat on the ledge within the lower bowl, therebY preventing accidental damaging contact between the bottom of one bowl and the lugs within a second bowl in which it is nested.

Additional advantages and objects of the invention will be apparent from or pointed out in the course of the detailed description of the preferred embodiment which follows.

BRIEF DESCRIPTION OF THE DRAWINGS

FIG. 1 is a plan view showing a bowl embodying the invention with a coiled guide wire temporarily stored therein;

FIG. 2 is a fragmentary section on the line 2—2 of FIG. 1 on a larger scale; and FIG. 3 is a fragmentary section on the line 3—3 of FIG. 1 showing how a plurality of the bowls of FIGS. 1 and 2 can be interfitted for shipment and/or storage.

DESCRIPTION OF THE PREFERRED EMBODIMENT

The bowl 10 shown in the drawing is readily molded of a plastic such as polyethylene, and it includes a lower portion 11 and an upper portion 12 of different diameters to facilitate nesting of a plurality of these bowls as shown in FIG. 3. A typical guide wire 13 for the purpose with which the invention is concerned may be as long as 60 inches, but it may readily be coiled as shown in FIG. 1 to fit in a circular bowl approximately 7½ inches in diameter, and it will normally include a hooked end 14 for providing a releasably anchored connection to the heart.

In a preferred embodiment of the invention, the upper portion 12 of the bowl 10 has an inner diameter of approximately 8¼ inches, and the lower bowl portion 11 has a sufficiently smaller inner diameter at its upper end to provide an annular ledge 15 approximately 5/32 inch in radial width. A plurality of lugs 20 extend radially inwardly from the inner periphery o this ledge 15. Satisfactory results have been obtained with six of these lugs 20 equally spaced around the inner periphery of the ledge 15, and with each lug having a width and radial dimension of approximately ¼ inch. In addition, the lower bowl portion 11 is bowl-shaped in axial section so that its inner surface 22 is of minimum diameter across the bottom wall 23 of the bowl, a difference of the order of ¼ inch between the minimum and maximum inner diameters of the wall portion 11 having been found satisfactory for the purposes of the invention as further described below.

In use, the bowl 10 is filled with a heparin solution 25 to a depth which will at least cover the ledge 15 and lugs 20. The wire 13 is then coiled to a diameter slightly less than that of the bowl portion 11 and is inserted therein below the lugs 20. Its natural springiness will then cause the wire to expand against the surface 22 of the bowl portion 11, and since the diameter of this surface increases from bottom to top, the wire will tend to continue expanding until it rises into contact with the lugs 20, thereby making it easier for the surgeon to grasp the wire for withdrawal from the bowl 10 than might be the case if the wire remained on the bottom of the bowl. The upper portion 12 of the bowl may also be somewhat frustoconical or bowl-shaped to facilitate its removal from the mold in which it is formed.

The shape and dimensions of individual lugs 20 are not critical, but they have practical limitations in that they should not interfere with manual withdrawal of the coiled wire without danger of its kinking, and the dimensions noted above have been found satisfactory from this standpoint. Further, the undersurface 26 of each lug should be curved upwardly and radially inwardly from its junction with the inner surface of the wall portion 11, as illustrated in FIG. 2. Thus when the surgeon grasps the coiled wire to withdraw it from the bowl, the coils will readily slip inwardly of the bowl along undersides of the lugs and then upwardly out of the bowl without the possibility of catching on any of the lugs such as could cause kinking of the wire. In addition, all edges of each lug are rounded, as shown at 27, to prevent possible cutting of the glove on the surgeon's hand reaching into the bowl to obtain the wire.

It is important for practical reasons that the individual bowls 10 be of such construction that they can readily and safely be stacked, e.g. six or more, for purposes of shipment and storage. For this purpose, the lower portion 11 of each bowl is provided on its outer surface with a plurality of circumferentially spaced ribs 30 extending axially from the bottom of the bowl to the lower surface of the ledge 15, satisfactory results having been obtained with six of these ribs equally spaced around the bowl.

The radial dimension of each of the ribs 30 should be such that the diameter of the bottom end of the bowl measured across two of these ribs is just enough less than the outer diameter of the ledge 15 to set one bowl inside another to the point where the bottom edges of the ribs 30 seat on the ledge 15. This relationship provides positive assurance against cocking of one bowl inside another to the extent that damage to any of the lugs 20 in the lower of the two bowls can occur, while at the same time facilitating separation of stacked bowls as well as withdrawal of each bowl from the mold wherein it is formed.

While the article herein described constitutes a preferred embodiment of this invention, it is to be understood that the invention is not limited to this precise article, and that changes may be made therein without departing from the scope of the invention which is defined in the appended claims.

What is claimed is:

1. Temporary storage means for retaining a coiled guide wire for introducing a catheter into the heart of a patient, comprising:

(a) a bowl having a wall of cylindrical section, predetermined height and an inner radius which will accommodate such guide wire in coiled form,
    (b) lug means projecting inwardly from the inner surface of said bowl wall at a position intermediate the top and bottom of said wall to define a space therebelow,
    (c) said lug means being of sufficient radial extent to retain such coiled wire therebelow immersed in a treating solution of a depth reaching said lug means while providing ready access to such wire for removal and use, the upper portion of said bowl wall above the level of said lug means is of a sufficiently larger inner diameter than the outer diameter of the lower portion of said wall below said lug means to provide for nesting of a plurality of said bowls for shipment and/or storage; and
    (d) means on the outer surface of said lower portion of said bowl for preventing said lower portion of the upper of two nesting said bowls from entering said lower portion of the lower of said two nesting bowls.

2. Storage means as defined in claim 1 wherein said lug means comprises a plurality of lug members located in circumferentially spaced relation around the inner surface of said bowl, each of said lug members being of limited width to provide spaces therebetween for ready manual access to such wire for removal thereof from said bowl.

3. Storage means as defined in claim 2 wherein the undersurface of each of said lug members is curved upwardly and radially inwardly from said inner surface of said bowl to facilitate removal of such wire from therebelow.

4. Storage means as defined in claim 3 wherein all exposed edges of each of said lug members are rounded to protect against accidental cutting of the glove on the hand of a surgeon reaching into said bowl to remove such wire therefrom.

5. Storage means as defined in claim 1 wherein the inner diameter of said lower bowl portion is sufficiently smaller than the inner diameter of said upper bowl portion as to provide an annular ledge therebetween, and said preventing means comprises projections on the outer diameter of said lower portion of said bowl proportioned to engage said inner diameter of a second bowl in nested relation therewith and to seat on said ledge in said second bowl.

6. Storage means as defined in claim 6 wherein said projections comprise circumferentially spaced ribs extending axially on the outer surface of said lower portion of each of said bowls.

* * * * *